United States Patent
Roseman (10) Patent No.: US 12,005,068 B2
(45) Date of Patent: *Jun. 11, 2024

(54) FORMULATION INCLUDING DOXYCYCLINE HYCLATE AND METHOD FOR ADMINISTERING THE SAME

(71) Applicant: Bruce Roseman, White Plains, NY (US)

(72) Inventor: Bruce Roseman, White Plains, NY (US)

( * ) Notice: Subject to any disclaimer, the term of this patent is extended or adjusted under 35 U.S.C. 154(b) by 921 days.

This patent is subject to a terminal disclaimer.

(21) Appl. No.: 17/022,294

(22) Filed: Sep. 16, 2020

(65) Prior Publication Data

US 2021/0015832 A1     Jan. 21, 2021

Related U.S. Application Data (63) Continuation of application No. 16/021,738, filed on Jun. 28, 2018, now Pat. No. 10,821,121.

(60) Provisional application No. 62/529,252, filed on Jul. 6, 2017.

(51) Int. Cl.
| | | |
|---|---|---|
| A61K 31/65 | (2006.01) | |
| A61K 9/00 | (2006.01) | |
| A61K 9/107 | (2006.01) | |
| A61K 9/14 | (2006.01) | |
| A61P 25/02 | (2006.01) | |

(52) U.S. Cl.
CPC ............ *A61K 31/65* (2013.01); *A61K 9/0014* (2013.01); *A61K 9/107* (2013.01); *A61P 25/02* (2018.01)

(58) Field of Classification Search
CPC ...... A61K 31/65; A61K 9/0014; A61K 9/107; A61P 25/02
See application file for complete search history.

(56) References Cited

U.S. PATENT DOCUMENTS 10,821,121 B2 * 11/2020 Roseman ................ A61P 25/02

OTHER PUBLICATIONS

Biondi DM. Is migraine a neuropathic pain syndrome? Curr Pain Headache Rep. Jun. 2006;10(3):167-78. doi: 10.1007/s11916-006-0042-y. PMID: 18778570. (Year: 2006).*

Scrivani SJ, Keith DA, Kaban LB. Temporomandibular disorders. N Engl J Med. Dec. 18, 2008;359(25):2693-705. doi: 10.1056/NEJMra0802472. PMID: 19092154. (Year: 2008).*

Papich MG, Davidson GS, Fortier LA. Doxycycline concentration over time after storage in a compounded veterinary preparation. J Am Vet Med Assoc. Jun. 15, 2013;242(12):1674-8. doi: 10.2460/javma.242.12.1674. PMID: 23725430. (Year: 2013).*

* cited by examiner

*Primary Examiner* — Mark L Shibuya
*Assistant Examiner* — Kevin S Martin
(74) *Attorney, Agent, or Firm* — Marvin Feldman, Esq.; NOLTE LACKENBACH SIEGEL (57) ABSTRACT

A topical formulation for transdermal delivery of sub-acute does of doxycycline hyclate to treat pain and inflammation may include: a base suspension; and doxycycline hyclate. The doxycycline hyclate is mixed with the base suspension in a proportion such that the formulation lacks any antibiotic effect and the concentration of doxycycline hyclate is between 200 and 600 mg/g inclusive. A method of applying the formulation is also disclosed.

17 Claims, 10 Drawing Sheets

FORMULATION INCLUDING DOXYCYCLINE HYCLATE AND METHOD FOR ADMINISTERING THE SAME

CROSS REFERENCE TO RELATED APPLICATIONS

The present application is a Continuation of U.S. application Ser. No. 16/021,738, filed Jun. 28, 2018, now U.S. Pat. No. 10,821,121, and claims priority thereto, claims priority and the benefit of U.S. Provisional Application Ser. No. 62/529,252, filed Jul. 6, 2017, the entire contents of which applications are hereby incorporated in their entireties by reference.

BACKGROUND

Technical Field

The present invention generally relates to a medical composition and the use of said medical composition. More particularly, the present invention relates to a topical formulation for the transdermal delivery of sub-acute doses of doxycycline hyclate for the treatment of pain from non-chronic conditions.

Description of the Related Art

Doxycycline has the potential to reduce various forms of debilitating pain stemming from inflammation. Doxycycline is in the antibiotic drug class of tetracyclines, which have a broad spectrum of antibiotic action. Doxycycline is taken to treat bacterial infections in all parts of the body. It stops the growth and spread of bacterial infections by halting the growth of bacteria. doxycycline accomplishes this by binding to the bacteria's 30S ribosomal unit, thereby preventing translation of proteins, thereby preventing the bacteria from making its proteins and killing the bacteria.

Some uses of doxycycline have included treating acne, which is caused by bacteria that clogs pores, may be treated by taking doxycycline orally and administering it systemically. Currently, there is no delivery system for delivering doxycycline locally or topically to the point of the infection. Systemic delivery has inherent drawbacks and disadvantages because the medication is delivered to areas of the body that do not need it and bacteria which may be beneficial are killed.

At most dose level, doxycycline functions as an antibiotic medication. However, at particular dosage levels, doxycycline can instead be used to reduce inflammation as is recognized in the present disclosure. At sub-acute or at very low doses, the antibacterial mechanism does not function and the drug can then be administered for anti-inflammatory use without the worry of disturbing bacteria such as healthy bacteria in the body or creating antibiotic resistance. This is an important health consideration as inhibiting the creation of "super bugs" that are resistant to current antibacterial medications is a public interest concern. Moreover, the preserving healthy bacteria and maintaining the body's microbiome at an equilibrium state, particularly in the digestive system, is desirable. Currently, however, doxycycline is not administered at sub-acute dosages that do not have an antibiotic effect. The human body's immune response to any damage or impairment is to send aid to that affected body part. As various molecules such as cytokines, interleukins, white blood cells, and others are sent to the affected area, the affected area swells. The purpose of such molecules being created and sent to the affected area is to repair the damage. However, this also initiates the process of inflammation. High concentrations of such pro-inflammatory molecules can offset the homeostatic equilibrium in the area and cause more harm than good.

One particularly damaging molecule is matrix metalloproteinase (MMP), which is an extracellular matrix destroying protein. Although MMPs are needed in the immune response, an overflow can cause the degradation of the extracellular matrix of healthy cells as well. The body's own regulator to these molecules, which are known as Tissue Inhibitor of Metalloproteinase (TIMPs) are not made in sufficient quantity to create the needed balance of MMPs in the body. The present disclosure recognizes that doxycycline at sub-acute doses have been shown to inhibit the activation of MMPs and thus cease the unnecessary and harmful destruction of the extracellular matrix (ECM).

Some patients undergoing treatments may experience pain from such treatments. For example, cancer patients undergoing chemotherapy have to endure the painful side effects of their treatment. This pain can develop in the form of peripheral neuropathy, which hyper-sensitizes the nerves in the peripheral extremities. This mechanism is caused by the pro-inflammatory response to the chemical agents building up around the nerves. Although chemical agents cannot pass the blood-nerve barrier, the destructive MMPs can pass the blood-nerve barrier. This results in the Protective myelin sheath covering the nerves to be degraded. This results in the patient experiences extreme sensitivity and debilitating pain that includes tingling, gravel-like, shocking sensations. This pain propagates from the most peripheral parts of the body, up the limbs depending on the toxicity and the duration of the chemical agents used. Currently, the pain medications that cancer patients take are systemic and may result in various unwanted side effects.

Accordingly, there is a need for an improved means of providing pain and inflammation relief.

ASPECTS AND SUMMARY OF THE INVENTION

A topical formulation for transdermal delivery of sub-acute does of doxycycline hyclate may include: a base suspension; and doxycycline hyclate. The doxycycline hyclate is mixed with the base suspension in a proportion such that the formulation lacks any antibiotic effect. In an embodiment, a suitable concentration of doxycycline hyclate is substantially within the range of 200-600 mg/ml inclusive, and preferably at substantially 400 mg/g. The base suspension may be an oil-in-water formulation and may have non-comedogenic and hypoallergenic properties.

A method of administering a topical formulation for transdermal delivery of sub-acute does of doxycycline hyclate, comprising: providing the formulation, the formulation comprising: a base suspension; and doxycycline hyclate, the doxycycline hyclate being mixed with the base suspension in a proportion such that the formulation lacks any antibiotic effect; and applying the formulation to a skin of a patient at an affected area. In an embodiment, a suitable concentration of doxycycline hyclate is substantially within the range of 200-600 mg/ml inclusive and preferably at substantially 400 mg/g. The base suspension may be an oil-in-water formulation and may have non-comedogenic and hypoallergenic properties.

The above and other aspects, features and advantages of the present invention will become apparent from the fol-

BRIEF DESCRIPTION OF THE DRAWINGS

A further understanding of the present disclosure can be obtained by reference to a preferred embodiment set forth in the illustrations of the accompanying drawings. Although the illustrated preferred embodiment is merely exemplary of methods, structures and compositions for carrying out the present disclosure, both the organization and method of the disclosure, in general, together with further objectives and advantages thereof, may be more easily understood by reference to the drawings and the following description. The drawings are not intended to limit the scope of this disclosure, which is set forth with particularity in the claims as appended or as subsequently amended, but merely to clarify and exemplify the disclosure.

For a more complete understanding of the present disclosure, reference is now made to the following drawings in which.

DETAILED DESCRIPTION OF THE PREFERRED EMBODIMENTS

Reference will now be made in detail to embodiments of the invention. Various operations may be described as multiple discrete operations in turn, in a manner that may be helpful in understanding embodiments of the present invention; however, the order of description should not be construed to imply that these operations are order dependent.

It has been observed in clinical studies as described herein that doxycycline has been found to not only function as an antibiotic, but as an immunomodulator as well. The immunomodulatory effects have been noted to only appear at very low concentrations of doxycycline. Matrix Metalloproteinase (MMP) is an enzyme that is produced by our body in the immune response to an infection or foreign entity. Our body overreacts to many situations and excessive MMPs are generated. These molecules and the body's immune response can lead to inflammation and pain. For example, MMPs have been found as a source of inflammation everywhere in the body so it is the common denominator. Applying the topical formulation where the inflammation is can reduce the pain by inhibiting the MMPs and their destructive effects.

Figure 1:
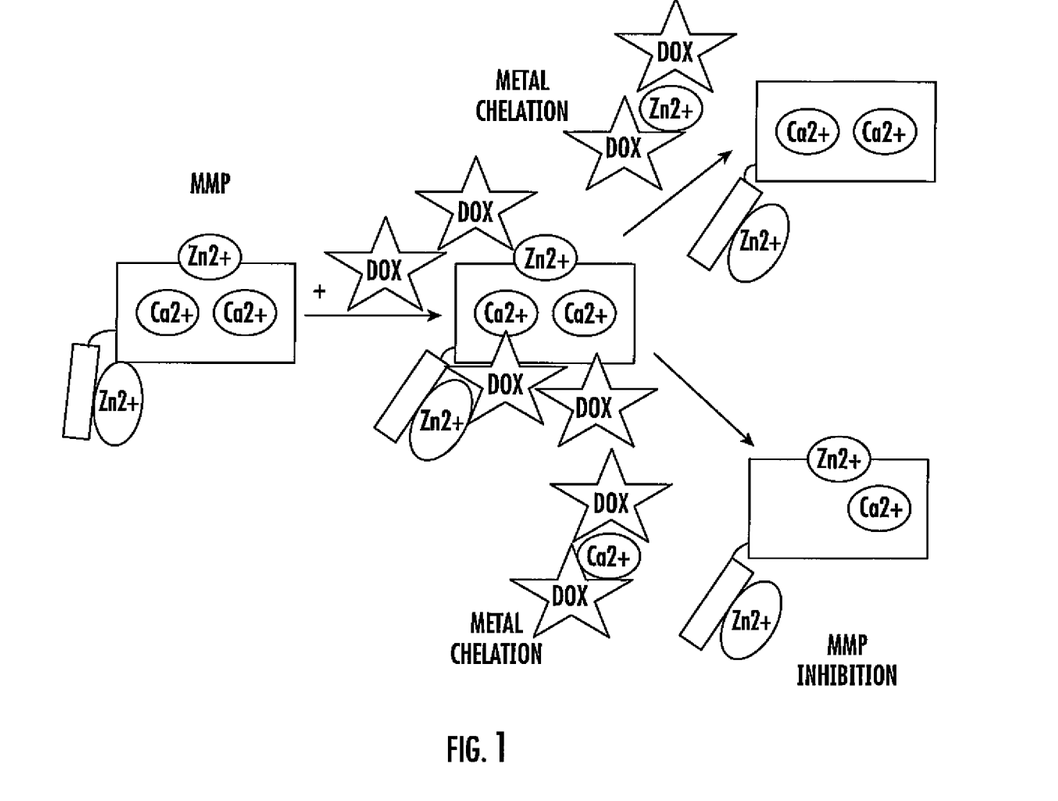
FIG. 1 is an illustration of the MMP inhibition caused by the application of doxycycline.

As shown in FIG. 1, doxycycline, at sub-acute doses, can also suppress transcription of the MMP genes through indirect inactivation of inducer molecules. Doxycycline effectively inhibits active MMPs by non selectively chelating the essential zinc and calcium cations found in the structure of MMPs. Once the cations have been essentially stripped away from the MMP enzyme, the active site is rendered inactive and of no use. The MMP enzyme cannot not bind to its intended substrate, the proteins comprising the extracellular matrix, without these key cations and thus the doxycycline molecule proves sufficient to inhibit the protein. MMPs and other pro inflammatory cytokines, such as interleukins and tumor necrosis factors, provide positive feedback loops upon each other. This is to say that once the substances are active they induce the synthesis of more molecules at the transcriptional level. Hence, doxycycline indirectly inhibits the active MMPs in the area, but also attenuates the production of more MMPs.

Doxycycline hyclate is the therapeutically active component of the present invention. In a preferred embodiment of the present invention, a topical formulation is disclosed including a base suspension, such as VERSAPRO cream or ELOBASE base or the like and doxycycline hyclate may be combined together and placed in an applicator tube, which can be stored at room temperature. The formulation uses sub acute doses of doxycycline, which is the immunomodulating dose and not the antibiotic dosage. VERSAPRO cream base and ELOBASE base have excellent drug compatibility with a wide range of active ingredients, making them suitable for the preparation of various pharmaceutical formulations in areas such as hormone replacement, pain management, and diabetic neuropathy. The formulation is prepared such that the concentration of doxycycline hyclate is such that it would not have an antibiotic effect while still treating pain and inflammation. The doxycycline hyclate may be in a concentration of 200-600 mg/g.

The bases may be oil-in-water formulations and may include such ingredients as: Purified Water, Glycerin, Ceteareth-20 and Cetearyl Alcohol. Caprylic/Capric Triglyceride, Behentrimonium methosulfate and Cetearyl Alcohol, Cetyl Alcohol, Petrolatum, Dimethicone, Potassium Phosphate, Dipotassium Phospate, Propylparaben, Sodium Lauroyl Lactylate, Disodium EDTA, Ceramide 3, Ceramide 6-II, Phytosphingosine, Cholesterol, carbomer, Xanthan Gum, Hyaluronic Acid, Ceramide I. Preferably, the bases exhibit strong drug compatibility and permeation, as well as non-comedogenic and hypoallergenic properties.

Figure 2:
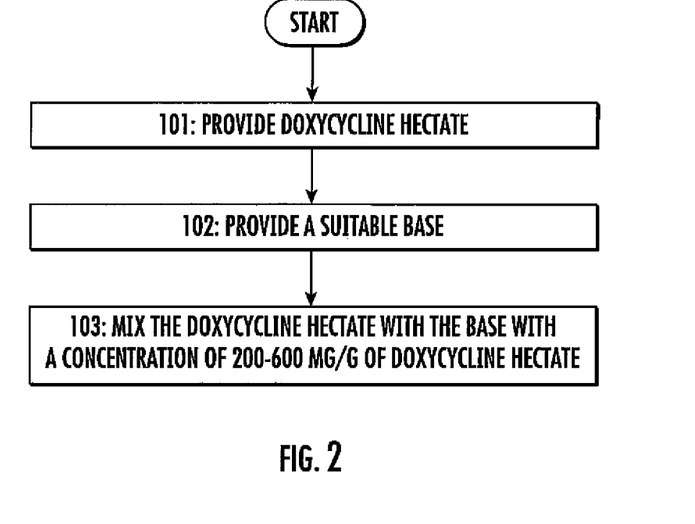
FIG. 2 is a flowchart illustrating the steps of preparing the therapeutic topical formulation in accordance with the present disclosure.

A method of preparing the presently disclosed therapeutic topical formulation is shown in the flowchart of FIG. 2.

A method of using the topical formulation may include squeezing it out of the applicator tube on spread onto, and preferably massaged into, an affected area of the patient's skin. The topical formulation is applied to affected areas. For example, for chemotherapy patients, the affected areas may include areas affected by chemotherapy induced painful peripheral neuropathy and/or drug induced polyneuropathy. The formulation can target the neuropathy in the extremities and relieve pain, tingling, shocking, hyperalgesia, and tension. This will allow cancer patients to endure treatment and continue it until completion. Furthermore, the topical formulation may be applied on joints exhibiting rheumatoid arthritis. This will allow for people to not be held back by their pain and do more. Other applications include application of the formulation on areas where there are swollen muscles, joints, and/or skin.

Various clinical studies, as shown in the below examples, have been performed on patients suffering from a variety of ailments, which show the efficacy of the present invention.

EXAMPLE 1

The following in vivo study of a human subject diagnosed with chemotherapy induced peripheral neuropathy demonstrated the efficaciousness of the disclosed treatment to alleviate pain symptoms as described herein.

A 75-year-old female patient complained of a tingling and burning sensation in her hands and feet that began shortly after she commenced chemotherapy. The patient had been previously diagnosed with primary peritoneal cervical cancer. While it was recommended that the patient undergo chemotherapy treatment for 18 weeks, the patient was unable to tolerate the side effects of the treatment after 11 weeks and ceased the treatment sessions. A biopsy that was performed shortly thereafter showed that the patient tested positive for carcinoma and a second chemotherapy regiment was started. The patient experienced the same side effects again and sought help to alleviate her pain.

The chemotherapeutic drugs that the patient received in the first regiment were platinum based. Platinum based drugs are known to cause peripheral neuropathy at a higher rate than non-platinum-based drugs. In addition, the patient was statistically more likely to suffer from peripheral neuropathy as she was both African American and a type II diabetic, both of which demographic groups have been shown to suffer from a greater incidence of peripheral neuropathy.

Upon physical examination by a practicing physician her gait was abnormal. Some of her symptoms included:
  (a) The patient had poor coordination. In particular, when the patient would stop looking at her feet, she would lose all sense of proprioception (i.e., her sense of the relative position of the body and strength of effort being employed in movement) was lost. The patient thus used a cane as she had trouble with stability.
  (b) The patient's sense of touch was poor. For example, the patient could not distinguish different textures as everything felt like silk to her.
  (c) The patient's sense of temperature was also poor. In particular, she had an altered temperature sensation. She was hyper-sensitized to slight changes in temperature.
  (d) There was an altered temperature sensation. She was hyper sensitized to slight changes in temperature. There was a loss of fine motor skills demonstrated by her inability to hold a small object or use it. She could not write, hold a phone, pick up change, buckle herself in a seat, or dress herself. In the absence of a stimulus, the patient felt the tingling, burning sensations in her hands and feet.
  (e) The patient's sensations would be exacerbated upon the introduction of a non-noxious stimulus.

Based on the above, the patient was diagnosed with chemotherapy induced peripheral neuropathy. The patient and her primary care physician attempted to address the symptoms, but had failed to do so. Some of the attempted medications were PERCOSET, GABAPENTIN, TYLENOL, ADVIL, LIDOCAINE, and CAPSAICIN. Numerous other over-the-counter medications were tried. Other attempted treatments included acupuncture. All such attempts failed to address the patient's symptoms.

The presently disclosed treatment was shown to be effective to alleviate pain stemming from the patient's chemotherapy induced peripheral neuropathy. In an embodiment of the presently disclosed treatment, a formulation of topical doxycycline hyclate suspension at a concentration of 400 mg/g. The prescribed administration included applying the formulation to the patient's hands and feet 2-3 times daily as needed for the pain. Each dose was 2 ml per foot, per hand, and per leg. Over the course of at least 18 months, the patient used the formulation every day during the remainder of the patient's second regiment of chemotherapy. The effect was immediate with a marked improvement of the patient's prior symptoms. In particular, immediately after applying the topical doxycycline for the very first time, the patient found relief in the tingling, burning feeling in the hands and feet. After a week, the patient was able to walk without looking at her feet. She was able to hold a pencil and write. She was able to pick up change. She could distinguish different textures when she grasped different objects.

After a month of the presently disclosed treatment which included topical doxycycline, the patient was able to drive for extended periods of time and resume a normal work routine. She regained her sense of proprioception and no longer needed to use a cane to walk. She was able to regain complete independence.

A couple of months after the presently disclosed treatment, the second regiment of chemotherapy ended and she was practically pain free and asymptomatic. She was able to finish the second round of chemotherapy in its entirety because her pain symptoms from the peripheral neuropathy were managed by the topical doxycycline.

The patient who would initially visited her doctor every week during the first two months of the treatment, but such visits were reduced to only routine checkups once every 2 to 3 months as the treatment greatly reduced her pain and she no longer needed medical attention to help alleviate her pain.

The patient continues to use the topical doxycycline on a daily basis. Her cancer has come back and she was put on her third round of chemotherapy.

Quantitatively, data was collected for at least 7 months on a "Treatment-Induced Neuropathy Assessment Scale" as shown in Table 1 below. The scale was proven in the scientific literature to be an effective tool to quantify change in symptoms presented by patients with peripheral neuropathy. The patient needed to assess her pain from a scale of 0 (non-existent) to 10 (unbearable pain). Throughout all the categories, the patient's pain went down. In some categories the pain was diminished altogether.

TABLE 1

Pain Rating for Patient in Example 6

| SYMPTOM | SEVERITY RATING BEFORE, TREATMENT (0-10, 0 = non-existant; 10 = extreme) | SEVERITY PAIN RATING AFTER TREATMENT (0-10, 0 = non-existant; 10 = extreme) |
|---|---|---|
| 1. Numbness in hands and feet | 7 | 0 |
| 2. Tingling in hands and feet | 8 | 3 |
| 3. Cramps in hands and feet | 3 | 0 |
| 4. Sensations of pins/needs in arms and legs | 8 | 2 |
| 5. Feeling of coldness in hands, feet, and fingers | 5 | 2 |
| 6. Hot burning sensations in hands and feet | 5 | 0 |
| 7. Swelling in hands and feet | 0 | 0 |
| 8. Sensation of electric shock | 4 | 0 |
| 9. Discomfort when touching things, generally | 9 | 2 |
| 10. Discomfort when skin comes in contact with wearable items including clothing, blankets, etc. | 9 | 3 |
| 11. Pain when touching cold things | 9 | 0 |
| 12. Trouble walking because of loss of feeling in legs and feet | 7 | 0 |
| 13. Difficulty with balance because of feeling in legs and feet | 6 | 0 |
| 14. Trouble grasping small objects | 9 | 9 |

Figure 3:
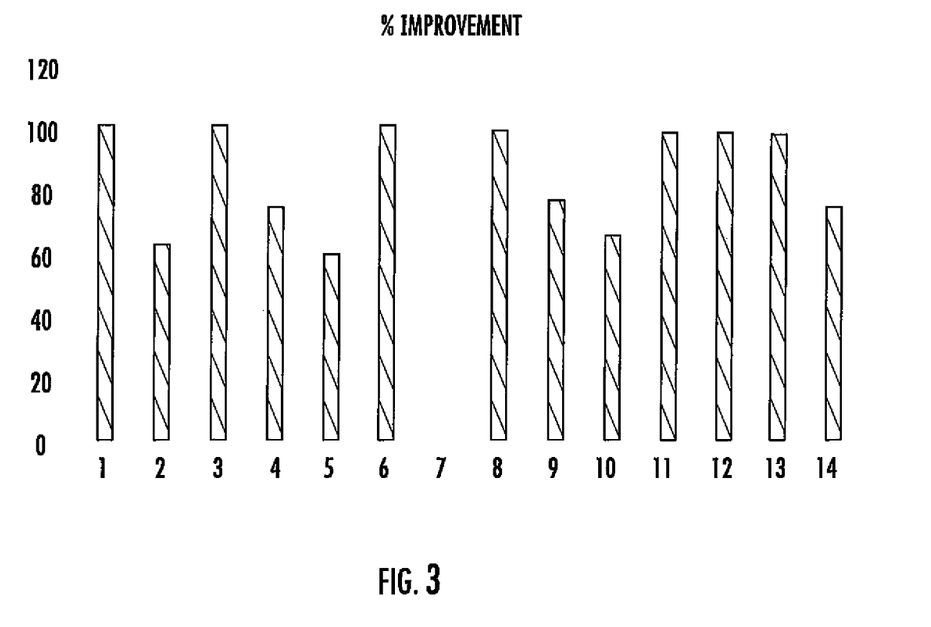
FIG. 3 is a graph illustrating various symptoms and the observed percentage improvement for those symptoms after administering the therapeutic topical formulation in accordance with the present disclosure.

FIG. 3 illustrates the percent improvement for each of the numbered symptoms 1-14 of Table 1 and provides a visual representation of the percent improvement that was realized for each symptom. All the symptoms showed marked improvement except for symptom 7 which did not exist prior to the treatment.

In addition, FIGS. 4-17 illustrate graphs in which levels of different types of pain, trouble, difficulty on a scale of 0 to 10 (0 being the best and 10 being the worst) is plotted on the y-axis over time (i.e., date month/day/year) on the x-axis. These graphs show the improvement in patient symptoms over time.

Figure 4:
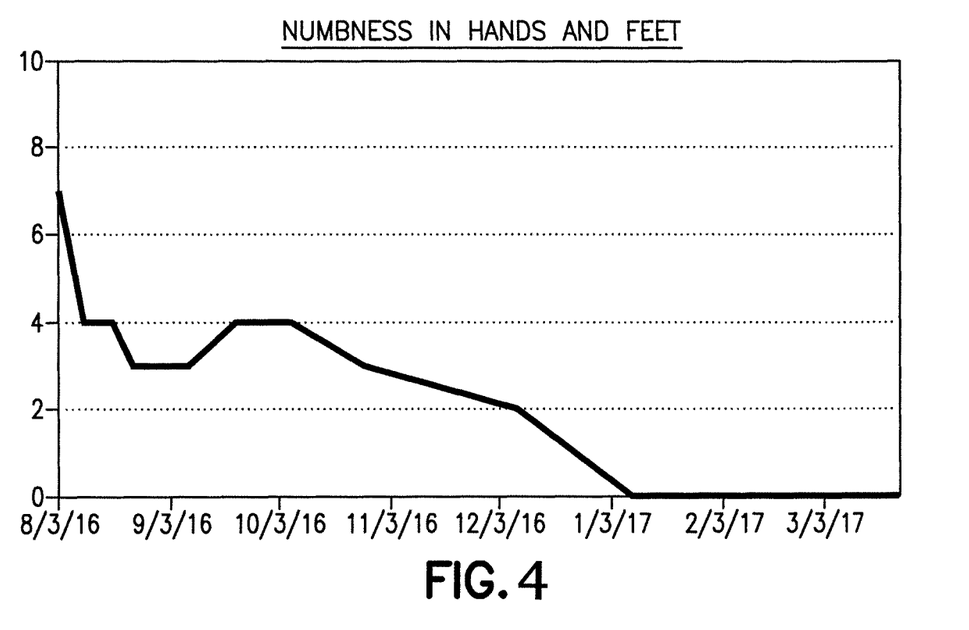
FIG. 4 is a graph illustrating levels of numbness in hands and feet over time.
Figure 5:
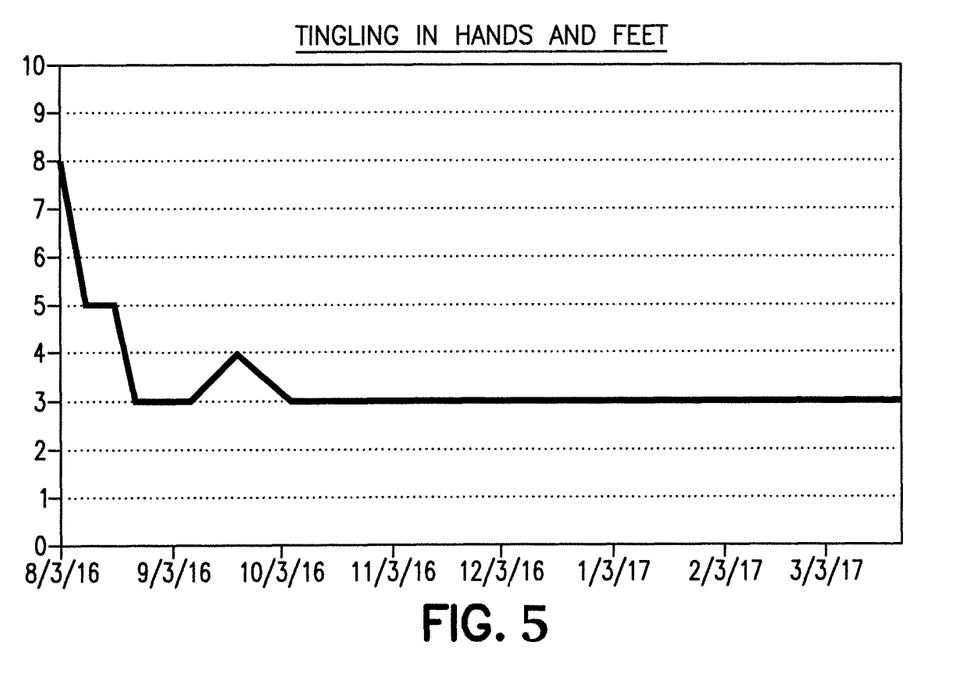
FIG. 5 is a graph illustrating levels of tingling in hands and feet over time.
Figure 6:
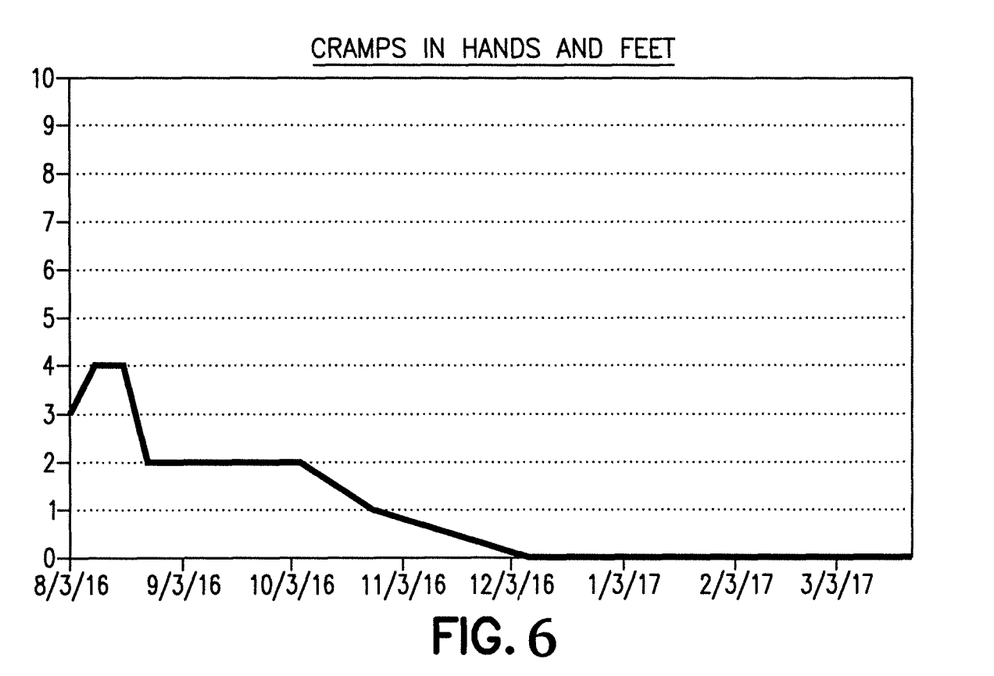
FIG. 6 is a graph illustrating levels of cramps in hands and feet over time.
Figure 7:
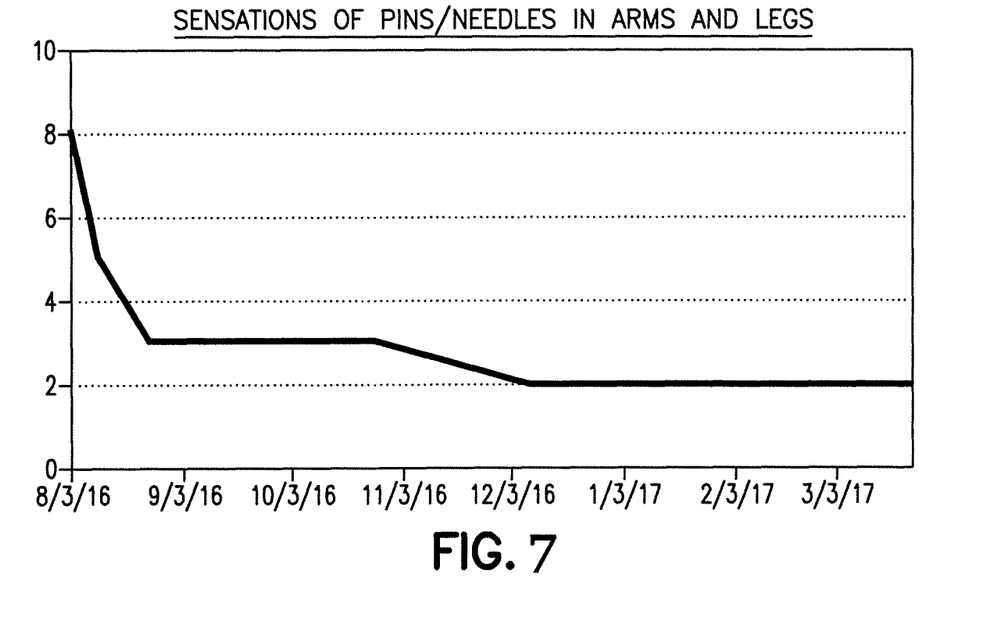
FIG. 7 is a graph illustrating levels of sensations of pins and needles in arms and legs over time.
Figure 8:
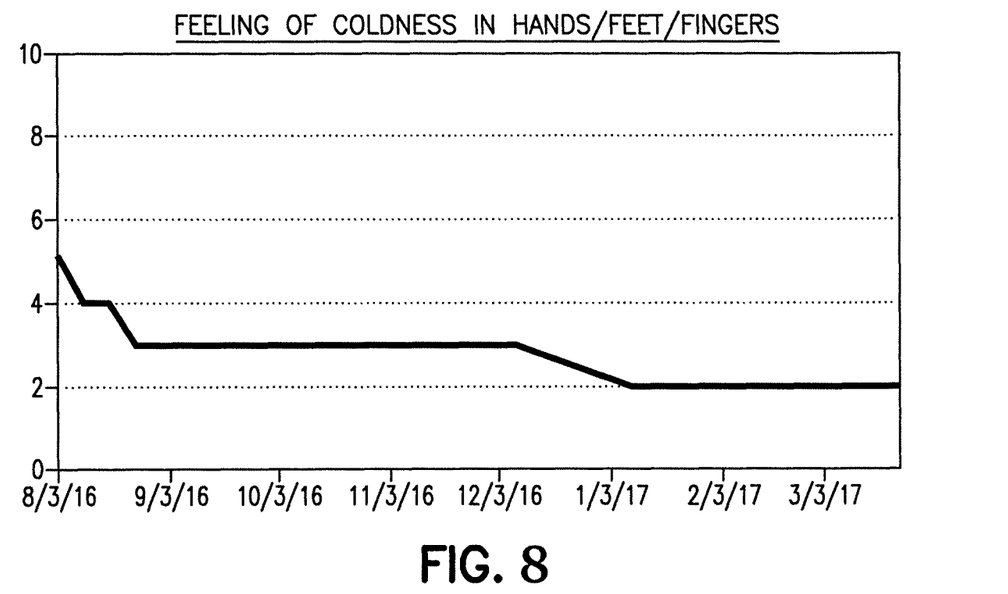
FIG. 8 is a graph illustrating levels feeling of coldness in hands/feet/fingers over time.
Figure 9:
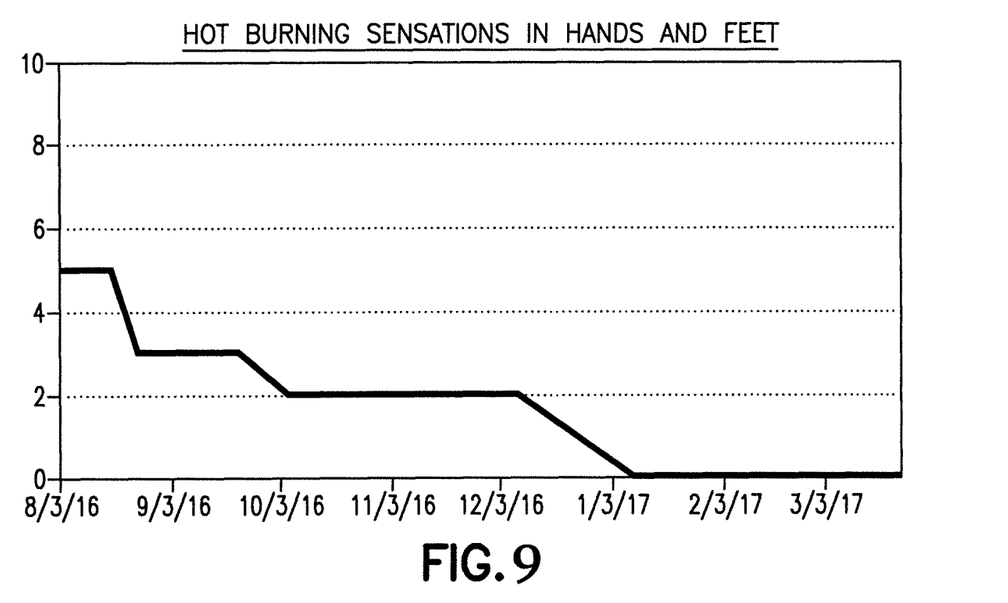
FIG. 9 is a graph illustrating levels of feeling of hot burning sensations in hands and feet over time.
Figure 10:
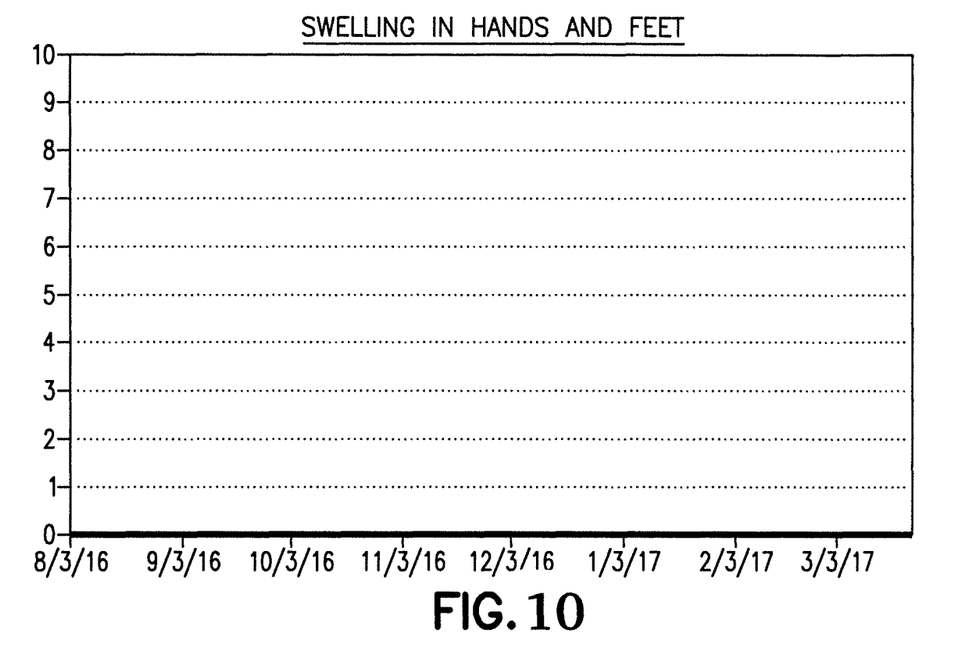
FIG. 10 is a graph illustrating levels of swelling in hands and feet over time.
Figure 11:
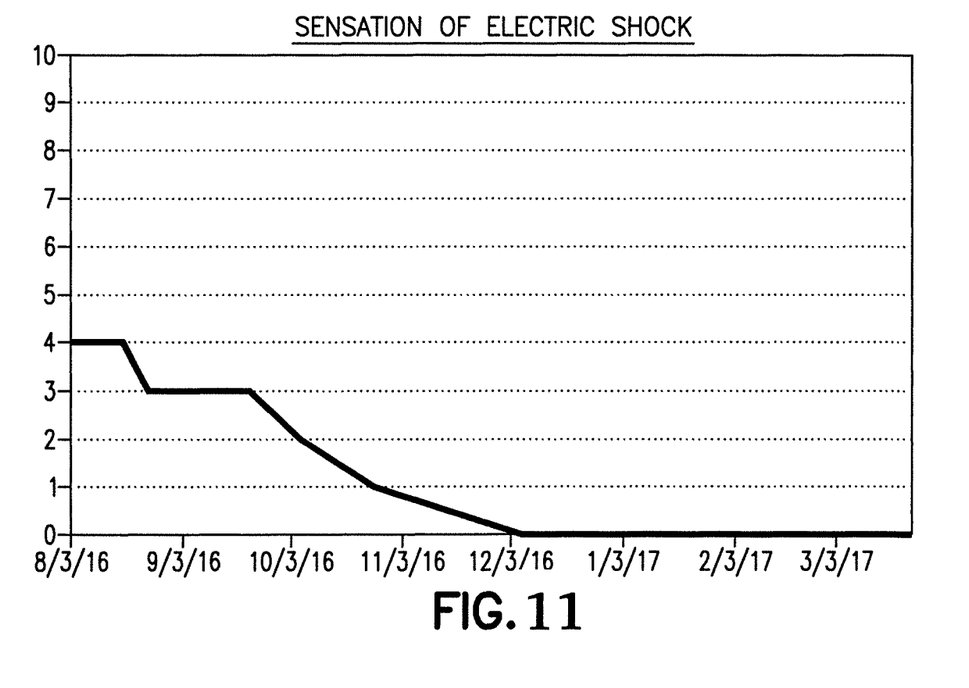
FIG. 11 is a graph illustrating levels of sensation of electric shock over time.
Figure 12:
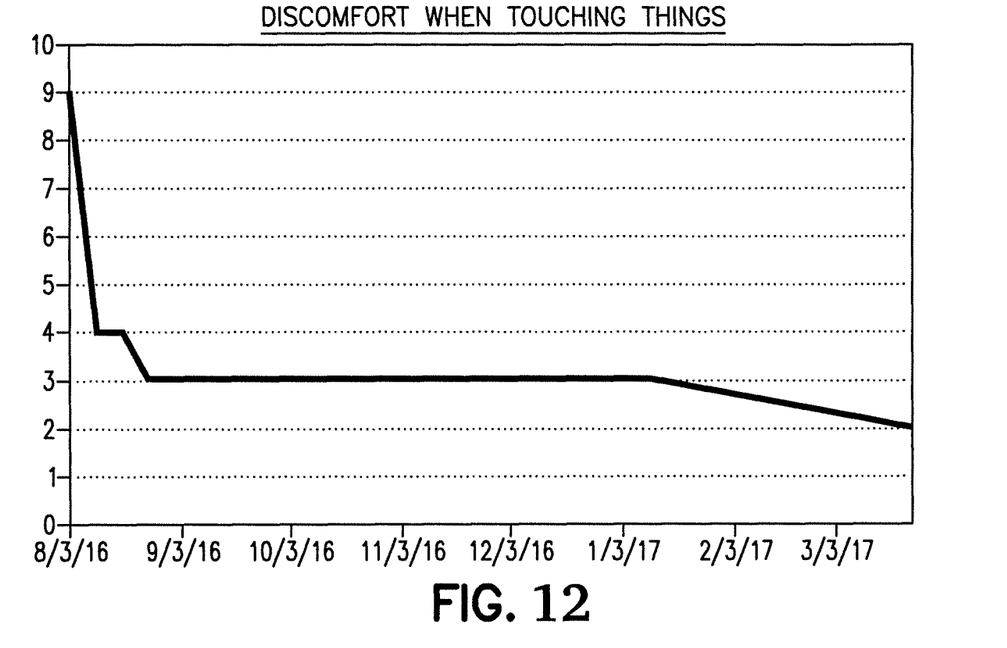
FIG. 12 is a graph illustrating levels of discomfort when touching things over time.
Figure 13:
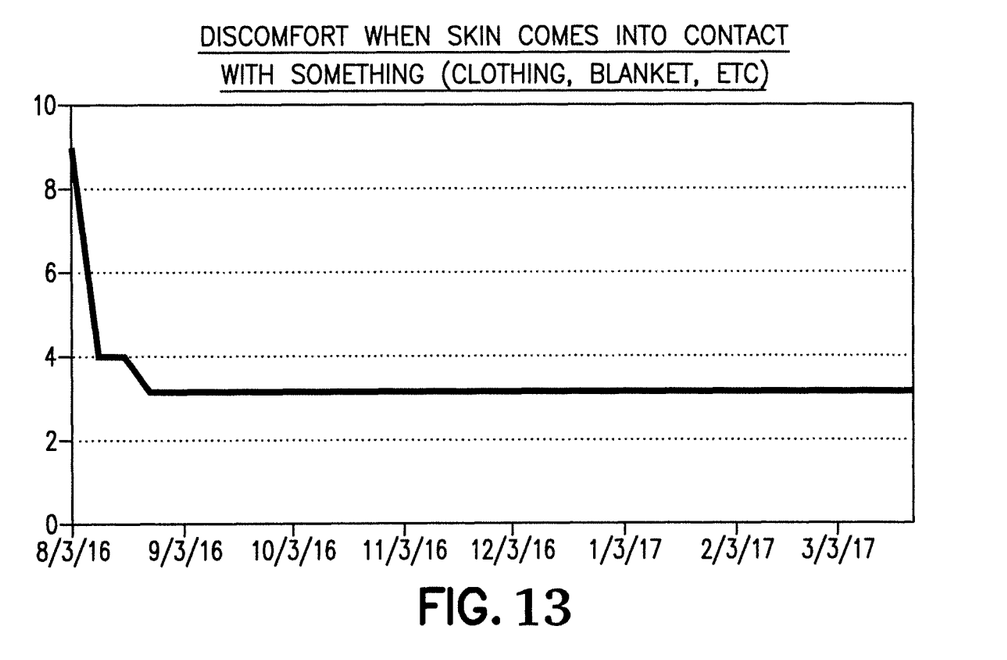
FIG. 13 is a graph illustrating levels of discomfort when skin comes into contact with something over time.
Figure 14:
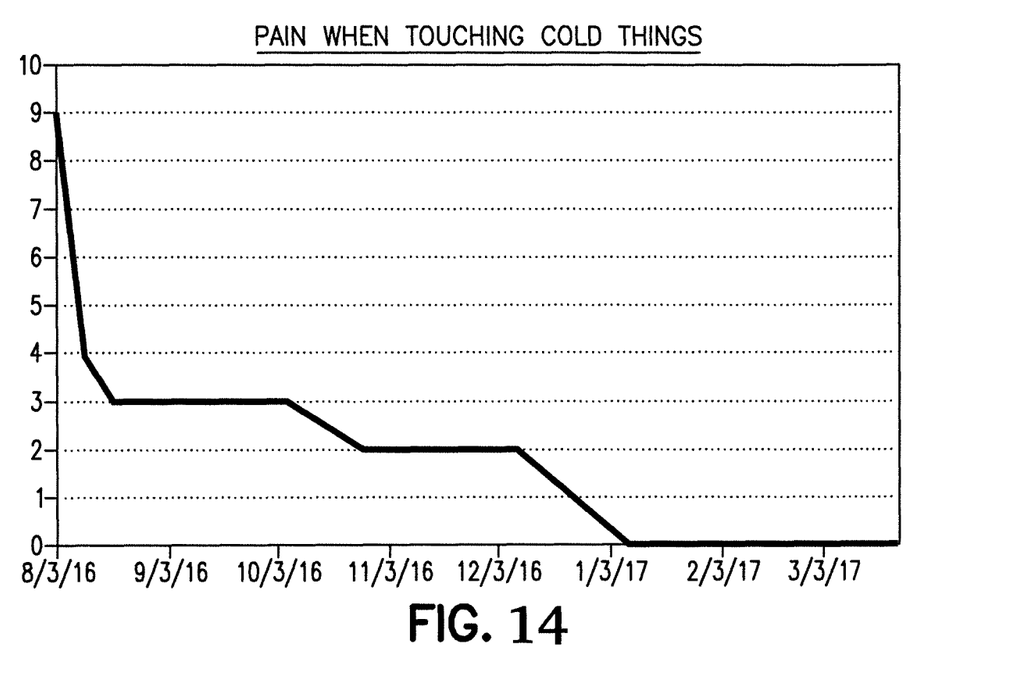
FIG. 14 is a graph illustrating levels of pain when touching cold things over time.
Figure 15:
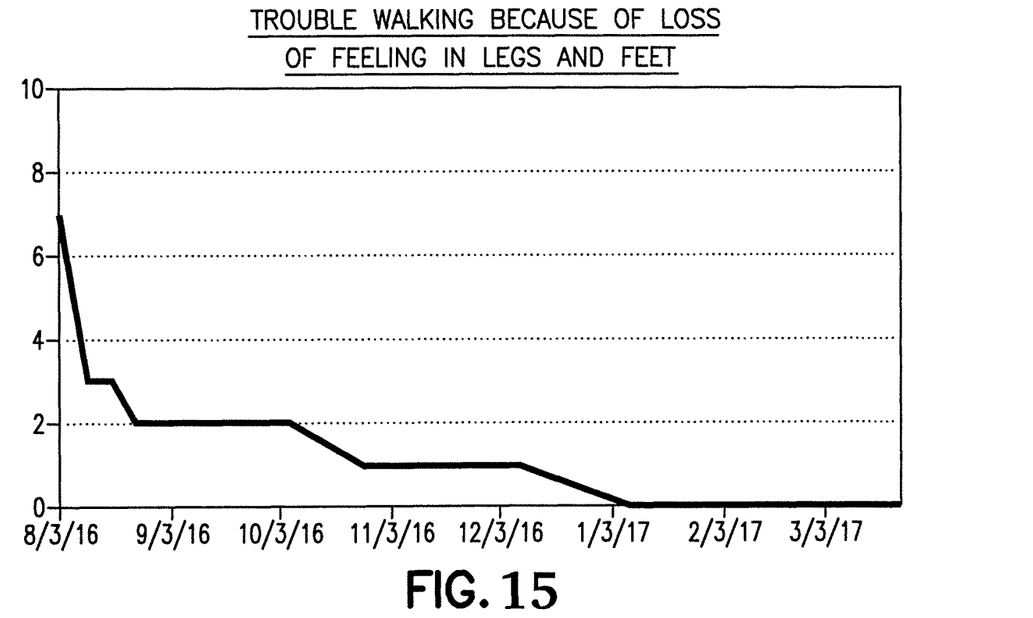
FIG. 15 is a graph illustrating levels of trouble walking because of loss of feeling in legs and feet over time.
Figure 16:
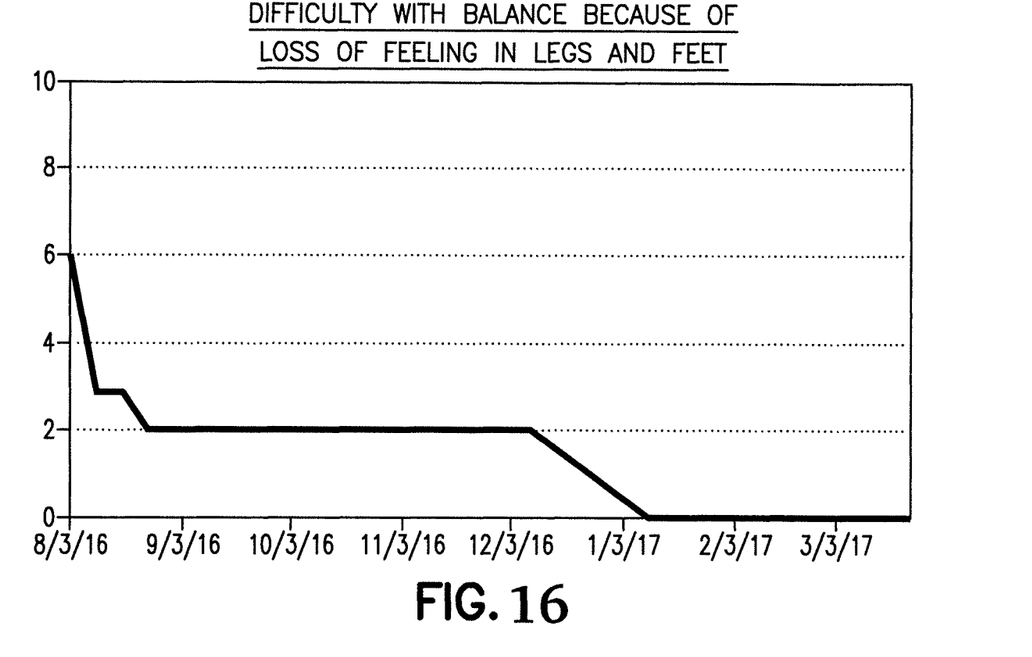
FIG. 16 is a graph illustrating levels of difficulty with balance because of loss of feeling in legs and feet over time.
Figure 17:
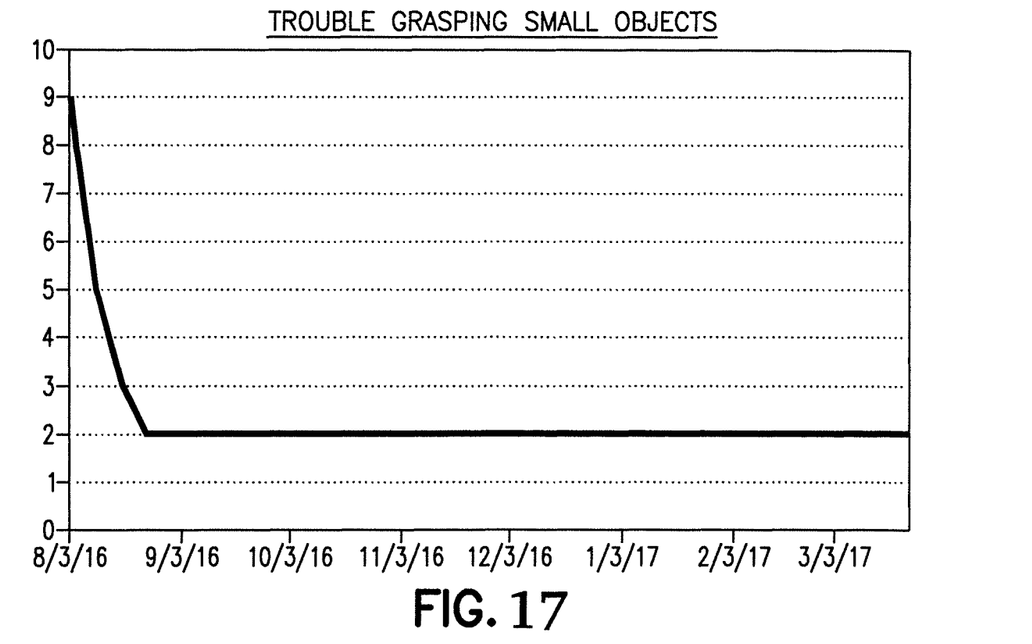
FIG. 17 is a graph illustrating levels of difficulty of trouble when grasping small objects over time.

In particular, FIG. 4 is a graph illustrating levels of numbness in hands and feet over time; FIG. 5 is a graph illustrating levels of tingling in hands and feet over time; FIG. 6 is a graph illustrating levels of cramps in hands and feet over time; FIG. 7 is a graph illustrating levels of sensations of pins and needles in arms and legs over time; FIG. 8 is a graph illustrating levels feeling of coldness in hands/feet/fingers over time; FIG. 9 is a graph illustrating levels of feeling of hot burning sensations in hands and feet over time; FIG. 10 is a graph illustrating levels of swelling in hands and feet over time; FIG. 11 is a graph illustrating levels of sensation of electric shock over time; FIG. 12 is a graph illustrating levels of discomfort when touching things over time; FIG. 13 is a graph illustrating levels of discomfort when skin comes into contact with something over time; FIG. 14 is a graph illustrating levels of pain when touching cold things over time; FIG. 15 is a graph illustrating levels of trouble walking because of loss of feeling in legs and feet over time; FIG. 16 is a graph illustrating levels of difficulty with balance because of loss of feeling in legs and feet over time; and FIG. 17 is a graph illustrating levels of difficulty of trouble when grasping small objects over time.

Accordingly, the numerical data show dramatic improvement for numerous symptoms including unwanted sensations and pain that the patient had experienced prior to undergoing the currently disclosed course of treatment.

EXAMPLE 2

The following in vivo study of a human subject diagnosed with osteoarthritis of the left knee.

A 53-year old female patient presented with complaints of left knee pain. The patient had been previously diagnosed with progressive osteoarthritis of the left knee. She had undergone two knee surgeries, but the pain came back within a few months. She next tried a series of ORTHOVISC (hyaluronan) injections with one adjunctive platelet rich plasma injection that also only temporarily stopped the pain. Her specialist said that the she was too young and too overweight for a full knee replacement surgery so she must rely on narcotic pain medications and hydrocortisone shots until she is a good candidate for the replacement surgery.

The patient began noticing that the hydrocortisone shots that once relieved her of pain for 3 months now only relieve her of pain for 3 weeks. She was concerned because she did not want to become addicted to her narcotic medication and decided to seek further help.

Upon physical examination by a practicing physician her gait was abnormal. She had foot drop due to the pain from her left knee, which also started causing her right foot to compensate for the left. This caused further damage and pain to the right foot. She experienced the most pain when bending or using the knee. The pain was present all day and night. She lost rest at night from not being able to sleep. When getting up from a sitting position she had to lift her left knee in order to not put any force on it, thus leaving the right leg to do all the work.

Some of the attempted medications to address the pain were Neurontin, Advil, Naproxen, Oxycodone, Hydrocodone, Extra Strength Tylenol, Motrin, and Acupuncture. In order to sleep throughout the night, the patient had to take at least 3 Extra Strength Tylenol and Motrin. During the day when she worked, if the pain was not tolerable, she would take TYLENOL (acetaminophen) and oxycodone.

The patient then began the currently disclosed treatment course to alleviate the pain from her osteoarthritis. As already discussed, the currently disclosed treatment is a topical doxycycline hyclate suspension at a concentration of 400 mg/g. She applied it to the knee twice a day. Each dose was approximately 4 ml per knee spread topically over the knee. Preferably, an application covers the affected area with a thin layer of the suspension. One application was before bedtime and the other was in the morning before going to work. The patient has been using it every day for the past month.

One week after the initiation of the presently disclosed topical formulation, the patient reported being able to sleep through the night. She didn't wake up from the pains in her knee. She also noted that she did not have to continue taking the Tylenol and Motrin before bedtime in order to sleep pain free. She stated that even when she got up in the middle of the night to use the restroom that she was able to get up, go, come back, and fall back asleep without pain. At work, the patient also noted that she was going up and down stairs more often than before. She said she used to climb up and down the stairs around 6 times in a day, but after introduction of the topical paste she could climb up and down the stairs around 8-10 times.

The patient was doing well and stopped returning for follow up as she was no longer experiencing pain after using the presently disclosed treatment.

EXAMPLE 3

The following in vivo study of a human subject diagnosed with central post stroke pain.

A 61-year old male patient presented with complaints of pain in the right foot that has progressively gotten worse. At the age of 50 the patient had suffered a stroke in the midbrain, which left him in a state of disability. He went to rehabilitation and was able to regain strength, stability, and mobility enough to return to working construction. The cause of the stroke was indeterminable since the patient was a healthy, working, active man with no prior medical history.

Half a year later the patient began feeling an itch in the toes of his right foot. This itch crawled up his leg and turned into a burning sensation after a month. The burning sensation is constant and if the affected body part touches anything lightly then the pain becomes intolerable. The patient has no sense of temperature in the affected right side. Seven years later the sensation crawled up his right leg, into his lower back, and down his right arm.

Upon physical examination by a practicing physician the patient had a slight foot drop in his gait. The most pain came from his right foot where the problem began. A light touch on the right foot causes excruciating pain, thus developing allodynia (i.e., pain from stimuli that do not normally provoke pain). Patient has lost all sense of temperature. He cannot tell whether a stimulus is hot or cold. The left eye turns in and the patient has surgery to correct it every 2 years. Without glasses he sees in multiples. The pain has taken away his rest at night due to the lack of sleep. The pain is noted to be unbearable at night.

The physician diagnosed a central post stroke pain that is known to get worse over time. It is difficult to manage due to the fact that the lesion causing sensitization of nerve cells is in the brain and not actually in the periphery.

The patient has tried over the counter pain medication, which was not effective.

The patient then began a new treatment course to alleviate the pain. This treatment is a novel formulation of topical doxycycline hyclate suspension at a concentration of 400 mg/g. He applied it to his foot once a day before bed. Each dose was 2 ml per foot. The patient used it every day for a month.

One week after the initiation of the presently disclosed topical formulation, the patient reported being able to sleep through the night. He didn't wake up from the pains and the patient reported being able to fall asleep within 20 minutes as opposed to hours prior to the disclosed treatment.

EXAMPLE 4

The following in vivo study of a human subject diagnosed with celiac disease.

A 65-year old female patient presented with constant hairline fractures. Onset of these fractures occurred with mild movement. 4 years prior to consult, the patient suffered 3 fractures simultaneously in her feet, of which 2 fully healed while a third did not.

Patient was in pain, could not walk, and was limping everywhere. The patient then began a new treatment course to alleviate the pain. This treatment is a novel formulation of topical doxycycline hyclate suspension at a concentration of 400 mg/g. She applied it to her foot once in the morning daily for 2-3 weeks. Each dose was 2 ml per foot.

After the course of treatment was finished, the patient reported to have substantially less pain. Her gait improved. She did not need a cast on her leg anymore. She regained independence. She never needed to use the topical doxycycline again and fortunately does not have recurring fractures to date.

EXAMPLE 5

The following in vivo study of a human subject diagnosed with multiple sclerosis.

A 55-year old male patient presented with excruciating pain in his quadriceps that extended down to his calves. The pain was triggered by the weekly injection of AVONEX (interferon beta-1a) the patient was taking in order to manage his multiple sclerosis. He could not sleep due to the pain. He often times took MOTRIN (ibuprogen), ADVIL (ibuprofen), and TYLENOL (acetaminophen) to try to alleviate the pain, but it was not as effective as he hoped.

The patient then began a new treatment course to alleviate the pain. This treatment is a novel formulation of topical doxycycline hyclate suspension at a concentration of 400 mg/g. Each dose was 4 ml per leg and 2 ml per arm/hands. He applied it to the affected areas when he was feeling the pain. He also applied it at work when he would get pains from handling complex machines such as nail guns.

The patient has been using the topical formulation when needed for at least a year and a half. The patient reports that the pain disappears after a few minutes of applying the cream. He now uses the cream right after taking his AVONEX (interferon beta-1a) injection in order to prevent the subsequent pain from occurring.

As a result of him being taken out of pain he is now able to work two physically demanding jobs and play on a sports team on the weekends.

EXAMPLE 6

The following in vivo study of a human subject diagnosed with osteoarthritis.

A 70-year old female patient presented with osteoarthritis in both knees due to a previous trauma years ago in her life. Her knees are in a constant state of pain and inflammation. She also has arthritis in the toe joints and shoulder.

The patient tried medications to relieve the pain. Some of the medications were Cox-2 inhibitors, TYLENOL (acetaminophen), Capsicum, and Meloxicam. These medications did not help manage the pain and the side effects had put her in a worse state than prior to taking them.

The patient then began a new treatment course to alleviate the pain. This treatment is a novel formulation of topical doxycycline hyclate suspension at a concentration of 400 mg/g. Each dose was 2 ml per knee. She applied it to the affected areas when she was feeling the pain. By the next day the patient feels minimal pain. She applies 1.5 ml of the topical doxycycline suspension daily for a week at night. She undergoes this treatment once every 4-6 months.

The patient stated that the pain from her knees went from a 6 to a 1 on a visual analogue pain scale where a 10 is the worst possible pain and 0 is when pain is nonexistent.

Qualitatively, the patient was not able to walk up or down stairs when she was in pain. After applying the topical cream, she was finding herself able to go up and down stairs. She was also able to start going to Pilates classes for 1-2 hours a week. She was able to go to the gym and leg press 100 pounds twice a week. Her range of motion in her arm and shoulder increased after applying the topical cream because she was not in pain anymore therefore she is able to use her arm for more daily activities.

EXAMPLE 7

The following in vivo study of a human subject diagnosed with idiopathic neuropathy.

A 70-year old male patient presented with idiopathic ice-cold burning sensations on the lateral surface area of the right shin/calf. The pain began 6 years ago and has stayed constant. The sensation does not spread, get worse, or get better with time.

He was unable to sleep consistently through the night. The patient woke up multiple times a night, got up and literally walked it off. The painful sensation was subdued with activity. He also felt relief when banging his shin with a PVC pipe at night. He did not take any medications for the pain because the patient stated that Ibuprofen and NSAIDs did not help. He eventually had to add extra layers of clothing to the affected area in order to "feel warmer" since the area always has a cold feeling. When placing a thermometer there was no physical temperature difference. The patient began going about his daily activities with compression socks and airplane blankets wrapped around his leg.

The patient then began a new treatment course to alleviate the pain. This treatment is the presently disclosed novel formulation of topical doxycycline hyclate suspension at a concentration of 400 mg/g. Each dose was 4ml to the affected right shin. He applied it topically to the affected areas when he was feeling the pain. He began applying it only once a day for 2 weeks before bed.

He reported sleeping on average 3 more hours a night after using the topical cream. He still got up in the middle of the night and had to walk off the pain at times, but it was noticeably less to him.

The patient had an adverse dermatological reaction to the cream when using the cream wrap. The patient applied the cream prior to bedtime, wrapped the leg with the wrap, and woke up in the middle of the night because a burning sensation so he washed it off. The next day he developed a rash, but it resolved on its own after a week. He continued to use the cream.

Additionally, examples 8-12 are provided illustrating the extent and breadth of the efficacy of the presently disclosed topical formulation.

EXAMPLE 8

A 65-year-old male suffering from overuse syndrome experienced extreme pain in his knees that prevented him from walking. After administering the topical formulation described herein, the patient is able to play tennis for 90 minutes.

EXAMPLE 9

A female aged 70, suffering from peritoneal cervical cancer who was experiencing hyperalgesia to the affected areas and a diminished quality of life (QOL) is no longer experiences pain and can now walk, work, and drive.

EXAMPLE 10

A 20-year-old male patient who was experiencing a cold sore on his lip had the inflammation decreased and the pain relieved.

EXAMPLE 11

A 12-year-old male suffering from a severe headache had his headache intensity significantly reduced within minutes.

EXAMPLE 12

A 30-year-old male suffering from post operation pain related to ankle reconstruction surgery had his pain relieved and was able to resume work.

The above examples provide evidentiary support of the efficacy of the presently disclosed treatment. Moreover, various conditions including those affecting, for example, the joints, skin, oral cavity can result in high levels of MMPs, which result in a corresponding increase in inflammation and pain, as well as, destruction of tissue. By lowering the level of MMPs, inflammation and pain can be correspondingly reduced and tissue can be preserved.

Joint conditions including, for example, trauma (e.g., sprains and/or strains), osteoarthritis, and rheumatoid arthritis result in high levels of MMP. It is now appreciated that the presently disclosed formulation when applied topically to the affected area treats the resultant inflammation and pain and allows tissue to regenerate.

Skin conditions such as EGFR inhibition, rashes, ulcers, tumors, cancer, burns, viral blisters, as well as anti-aging products, result in high levels of MMP. Topical application of the presently disclosed formulation to the affected area has been shown to reduce pain and inflammation.

Oral conditions such as periodontitis, gum disease, and tooth decay, as well as heart disease, which may be correlated to oral health, may also result in high levels of MMP. Topical application of the formulation to the affected area has been shown to reduce inflammation and also improve the health of the gums and a reduction in tooth decay. The subacute dosage of doxycycline hyclate acts as an anti-inflammatory by reducing the activities of the MMPs, which are responsible for the breakdown of alveolar bone, the tooth, and the soft tissues (i.e., the gingival) surrounding the tooth. In this embodiment, the topical formulation may be used as a toothpaste, for example, for applying and/or massaging the topical formulation within the oral cavity. The topical formulation may be used not only to treat pain but as a preventative measure against tooth decay and gum disease.

While the presently disclosed therapy has been shown to be effective to treat pain resulting from chronic conditions, the presently disclosed therapy is also effective to treat non-chronic pain that does not result from any particular condition. Moreover, it is advantageous that the presently disclosed therapy includes applying doxycycline hyclate in a sub-acute dosage that does not have any substantial antibiotic properties as it has been shown that where possible, it is best not to kill the body's natural bacteria as some of that bacteria may be beneficial and/or kill other bacteria that may needlessly become resistant to antibiotics. Thus, the present disclosure is uniquely advantageous As discussed chemotherapy patients often suffer from pain and inflammation because of the adverse side effects of the chemical agents used in their treatment. It has been observed that chemotherapy is more effective with fewer skin rashes, diseases and neuropathy, which might otherwise result as side effects.

The presently disclosed formulation would also help curb the Oxycontin epidemic as individuals suffering from Oxycontin addiction are attempting to alleviate their pain and inflammation symptoms. A reduction in their pain symptoms would correspondingly reduce their dependence on pain relievers such as Oxycontin as they can achieve a reduction in pain and inflammation by taking the presently described formulation transdermally.

Other patients who would benefit from the presently described formulation include burn patients who suffer from both pain and inflammation. The presently described formulation may be administered transdermally at or near the affected areas including the location of the burn wounds.

Still other patients who would benefit from the presently describe formulation are those suffering from wounds or ulcers such as diabetic ulcers of the extremities (e.g., legs and feet). Similarly, the presently described formulation may be administered transdermally to the affected areas by applying and massaging it into those areas.

Advantageously, the topical application of the formulation has none of the adverse side effects of a systemic delivery, which may include heart side effects. The formulation described herein includes the active ingredient of doxycycline hyclate preferably in a subacute dosage such that it would not have an antibiotic effect such ranges of the concentration of doxycycline hyclate include 200 mg/g, 400 mg/g, and 600 mg/g. However, it is to be understood that any subacute dosage of doxycycline hyclate such that the antibiotic effects of the substance are not experienced would be within the scope and spirit of the present application. It is further understood that the preferred method of administering the substance is transdermally such that the patient does not experience the ill effects of a systemic delivery. It is further understood that doxycycline is the active ingredient in the presently disclosed formulation and that, although referred to as Doxycyline hyclate in the various embodiments described herein, in other embodiments other forms of doxycycline including, for example, doxycycline monohydrate, doxycycline carrageenate, doxycycline calcium and doxycycline phosphate (fosfatex) may be suitable and used instead while remaining in the scope and spirit of the present disclosure.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. A method of administering a topical formulation for transdermal delivery of doxycycline hyclate for treating headache pain in a subject in need of such treatment, said method comprises:

(a) providing the formulation, the formulation comprising; doxycycline hyclate disposed in a suspension; wherein the doxycycline hyclate in a dose is transdermally deliverable at a portion of the skin evincing the pain, whereby the pain is diminished; and (b) applying a layer of the formulation to the skin evincing the pain.

2. The method of claim 1, wherein the doxycycline hyclate has a concentration in the suspension of between 200 and 600 mg/g.

3. The method of claim 1, wherein the doxycycline hyclate has a concentration in the suspension of 400 mg/g.

4. The method claim 1, wherein the suspension is an oil-in-water suspension.

5. The method of claim 1, wherein the suspension has non-comedogenic and hypoallergenic properties.

6. The method of claim 1, wherein the pain comprises severe headache pain.

7. A method of treating headache pain in a subject in need of such treatment, said method comprises: providing a topical formulation comprising doxycycline hyclate in a suspension, and applying the formulation to the skin evincing the headache pain.

8. The method of claim 7, wherein the doxycycline hyclate has a concentration in the suspension of between 200 and 600 mg/g.

9. The method of claim 7, wherein the doxycycline hyclate has a concentration in the suspension of 400 mg/g.

10. The method of claim 7, wherein the suspension is an oil-in-water suspension.

11. The method of claim 7, wherein the suspension has non-comedogenic and hypoallergenic properties.

12. A topical headache pain composition comprising doxycycline hyclate disposed in a suspension, wherein the doxycycline hyclate has a concentration of 400 mg/g.

13. A topical headache pain composition comprising doxycycline hyclate disposed in a suspension, wherein the suspension is an oil-in-water suspension.

14. The method of claim 1, wherein the pain comprises a neuropathy.

15. The method of claim 7, wherein the pain comprises a neuropathy.

16. The method of claim 1, wherein (b) further comprises applying the formulation adjacent a muscle evincing the pain.

17. The method of claim 7, wherein said applying further comprises applying the formulation adjacent a muscle evincing the pain.

* * * * *